United States Patent
Luke et al.

(10) Patent No.: US 6,921,827 B2
(45) Date of Patent: Jul. 26, 2005

(54) PROCESS FOR PREPARING 3-ARYL-BENZO{B} THIOPHENES

(75) Inventors: Wayne Douglas Luke, West Lafayette, IN (US); Heidi Ann Sanderson, Cody, WY (US); Hua Zheng, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 121 days.

(21) Appl. No.: 10/415,569

(22) PCT Filed: Nov. 14, 2001

(86) PCT No.: PCT/US01/42940

§ 371 (c)(1),
(2), (4) Date: Sep. 22, 2003

(87) PCT Pub. No.: WO02/42289

PCT Pub. Date: May 30, 2002

(65) Prior Publication Data

US 2004/0132775 A1 Jul. 8, 2004

Related U.S. Application Data

(60) Provisional application No. 60/253,212, filed on Nov. 27, 2000.

(51) Int. Cl.[7] ..................... C07D 409/00; C07D 333/52
(52) U.S. Cl. ........................ 546/281.1; 549/51
(58) Field of Search ........................ 549/51; 546/281.1

(56) References Cited

U.S. PATENT DOCUMENTS

| | | | |
|---|---|---|---|
| 4,075,227 A | 2/1978 | Jones | |
| 4,133,814 A | 1/1979 | Jones | |
| 4,358,593 A | 11/1982 | Jones | |
| 4,380,635 A | 4/1983 | Peters | |
| 4,418,068 A | 11/1983 | Jones | |
| 5,510,357 A | 4/1996 | Palkowitz | |
| 5,512,684 A | 4/1996 | Alt | |
| 5,523,416 A | 6/1996 | Alt | |
| 5,552,401 A | 9/1996 | Cullinan | |
| 5,629,425 A | 5/1997 | LaBell | |
| 5,723,474 A | 3/1998 | Palkowitz | |
| 5,731,327 A | 3/1998 | Luke | |
| 5,969,157 A | 10/1999 | Vicenzi | |
| 5,977,383 A | 11/1999 | Vicenzi | |
| 6,388,105 B1 * | 5/2002 | Vuligonda et al. | 549/471 |
| 6,403,172 B1 * | 6/2002 | Wingen et al. | 428/1.1 |
| 6,437,144 B2 * | 8/2002 | Junghans et al. | 548/183 |
| 6,472,531 B1 * | 10/2002 | LaBell et al. | 546/202 |
| 6,495,702 B2 * | 12/2002 | Honma et al. | 549/51 |
| 6,555,697 B1 * | 4/2003 | Schlama | 549/471 |

FOREIGN PATENT DOCUMENTS

| | | |
|---|---|---|
| WO | WO 01/09115 | 2/2001 |
| WO | WO 01/09116 | 2/2001 |
| WO | WO 02/42261 | 5/2002 |

OTHER PUBLICATIONS

Kim, A Facile Synthesis of 3–aryl–Substituted–Benzothiophenes via a Lewis Acid Mediated Cyclization of 2–Arylthio–Acetophenones, Tetrahedron Letters, vol. 40, p. 2909–2912 (1999).

* cited by examiner

*Primary Examiner*—Deborah C. Lambkin
(74) *Attorney, Agent, or Firm*—Gary M. Birch; Gilbert T. Voy

(57) ABSTRACT

The present invention relates to a process for preparing a compound of formula (I): which includes cyclodehydrating a compound of formula (II): in the presence of an acid activated clay or acid activated zeolite catalyst and in the presence of a suitable solvent

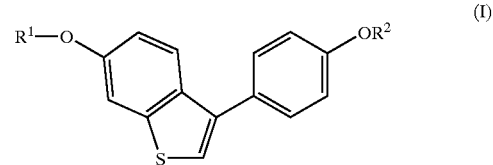

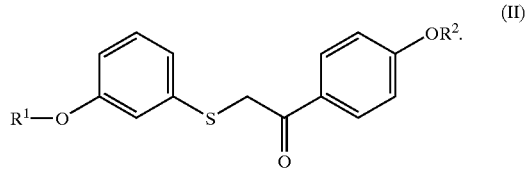

8 Claims, No Drawings

PROCESS FOR PREPARING 3-ARYL-BENZO{B} THIOPHENES

This application is 35 USC 371 of PCT/US01/42940, filed Nov. 14, 2001 which claims the benefit of U.S. Provisional application No. 60/253,212 filed Nov. 27, 2000.

BACKGROUND OF THE INVENTION

Compounds of the formula:

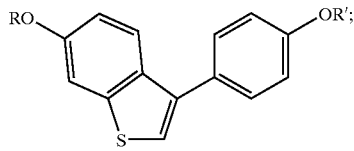

wherein R and R' are the same or different hydroxy protecting group; are intermediates to pharmaceutically active compounds (see, e.g., U.S. Pat. Nos. 4,075,227, 4,133,814, 4,418,068, 5,552,401 and 5,723,474).

According to the procedures described in the above mentioned patents and other literature references, these intermediates are constructed via an acid catalyzed cyclodehydration reaction of a compound of the formula:

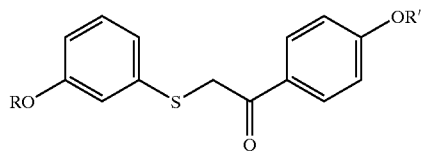

Said cyclodehydration reaction results in an initial mixture of 6- and 4-OR isomers (nomenclature refers to the position of the OR group on the benzothiophene ring) which lie in equilibrium with a pair of corresponding aryl migrated isomers. These isomers and their relationship to each other are illustrated below where the #(#) nomenclature refers first to the position of the OR group on the benzothiophene ring and refers second to the position of the phenyl-OR' group on the benzothiophene ring:

Initial Cyclodehydration Products

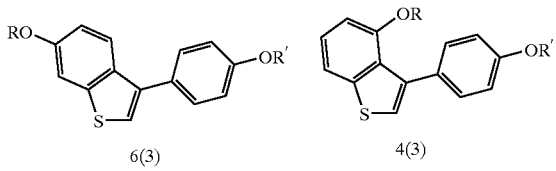

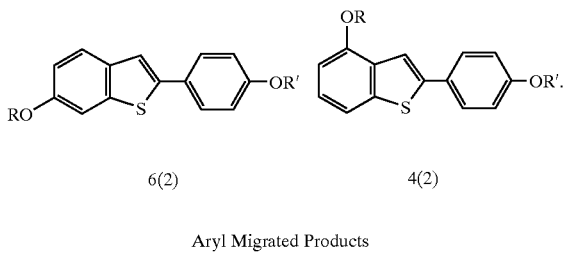

Aryl Migrated Products

The art teaches that the above cyclodehydration can be catalyzed with certain acids including mineral and organic acids such as polyphosphoric, phosphoric and methanesulfonic acid, acidic cation exchange resins such as Amberlyst 15, and Lewis acids such as boron trifluoride etherate (see, e.g., Tet. Let., 40:2909, 1999; Org. Proc. Res. & Dev., 3:56, 1999; and U.S. Pat. No. 's 4,358,593, 5,512, 684, 5,969,157 and 5,977,383). The use of said acids result in varying 6 to 4-OR isomer ratios and also vary in their amenability toward isolating the 3-aryl isomers, particularly the 6(3) isomer.

For example, when polyphosphoric, phosphoric or methanesulfonic acid is employed, and R and R' are both methyl, the 6 to 4-OR isomer ratio ranges from about 75:25 to about 80:20. Furthermore, when these acids are employed, it is difficult to isolate either of the initial cyclization products since the 2-aryl/3-aryl isomer equilibrium is quickly established and favors the 2-aryl isomer.

When Amberlyst 15 is employed, the rearrangement reaction is approximately fifty to a hundred times slower than the cyclization and hence the 3-aryl isomer can be isolated if desired. However, upon consumption of the cyclization starting material (about 7 hours when R and R' are both methyl and with a 10% weight loading of the Amberlyst 15 resin), a significant amount of the 3-aryl isomer (about 7.4%) has rearranged to the 2-aryl isomer. Similarly, when one of R or R' is hydrogen and the other is methyl about 8.1% of the 3-aryl isomer in both cases has rearranged to the 2-aryl isomer. Moreover, use of Amberlyst 15 affords about a 88:12 in situ mixture of 6 and 4-OR isomers when R and R' are methyl, a ratio of 88:12 when R is hydrogen and R' is methyl and 90:10 when R is methyl and R' is hydrogen.

Although the 3-aryl isomer is accessible when boron trifluoride is employed, in order to obtain reasonable yields the reaction must be run neat. Furthermore, use of this acid on a compound where R and R' are both methyl results in 6 to 4-OR isomer ratios comparable to that of polyphosphoric acid (about 6:1). Work-up and product isolation requires quenching and removing the acid via solvent extractions.

BRIEF SUMMARY OF THE INVENTION

The present invention relates to a process for preparing a compound of formula I:

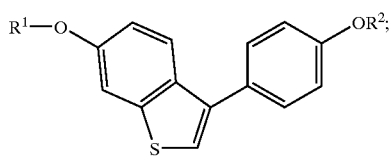

wherein:

$R^1$ and $R^2$ are independently hydrogen or a hydroxy protecting group; which includes cyclodehydrating a compound of formula II:

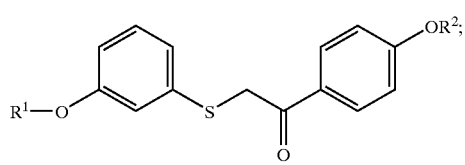

in the presence of an acid activated clay or acid activated zeolite catalyst and in the presence of a suitable solvent.

DETAILED DESCRIPTION OF THE INVENTION

General terms used in the description of chemical formulas bear their usual meanings. For example, the term "hydroxy protecting group" denotes a group understood by one skilled in the organic chemical arts of the type described in Chapter 2 of "Protective Groups in Organic Synthesis, 2nd Edition, T. H. Greene, et al., John Wiley & Sons, New York, 1991, hereafter "Greene".

Representative hydroxy protecting groups include, for example, $C_1$–$C_6$ alkyl and substituted $C_1$–$C_6$ alkyl, including methyl, ethyl, isopropyl, cyclopropyl, methoxymethyl, methylthiomethyl, tert-buylthiomethyl, (phenyldimethylsilyl)methoxymethyl, benzyloxymethyl, p-methoxy-benzyloxymethyl, tert-butoxy-methyl; ethoxyethyl, 1-(2-chloroethoxy)ethyl, 2,2,2-trichloroethoxymethyl, and 2-(trimethylsilyl)ethyl; phenyl and substituted phenyl groups such as p-chlorophenyl, p-methoxyphenyl, and 2,4-dinitrophenyl; benzyl groups; alkylsilyl groups such as trimethyl- triethyl- and triisopropylsilyl; mixed alkylsilyl groups such as dimethylisopropylsilyl, and diethylisopropylsilyl; acyl protecting groups such as those of the general formula $COC_1$–$C_6$ alkyl or COAr; and esters of the general formula $CO_2C_1$–$C_6$ alkyl, or $CO_2Ar$, where Ar is phenyl or substituted phenyl as described above.

The term "suitable solvent" refers to any solvent, or mixture of solvents, inert to the ongoing reaction that sufficiently solubilizes the reactants to afford a medium within which to effect the desired reaction. Suitable solvents include methylene chloride, chloroform, 1,2-dichloroethane, diethyl ether, acetonitrile, ethyl acetate, 1,3-dimethyl-2-imidazolidinone, 1,4-dioxane, tetrahydrofuran, toluene, chlorobenzene, N-methylpyrrolidinone, toluene, xylene, halophenyl solvents such as chlorobenzene, etheral solvents such as glyme, diglyme and ethyleneglycol diether ether, mixtures thereof, and the like. Toluene is a preferred solvent.

The term "acid-activated clay" refers to clays that are derived from the naturally occurring ore bentonite or the mineral montmorillonite and includes materials prepared by calcination, washing or leaching with mineral acid, ion exchange or any combination thereof including materials which are often called montmorillonites, acid-activated montmorillonites and activated montmorillonites. These clays contain both Bronsted as well as Lewis acid active sites with many of the acidic sites located within the clay lattice. Such clays include, but are not limited to the materials denoted as, montmorillonite K10, montmorillonite clay, clayzic, clayfen, the Engelhardt series of catalysts related to and including X-9107, X9105, Girdler KSF, Tonsil and K-catalysts derived from montmorillonite including but not limited to K5, K10, K20 and K30, KSF, KSF/O, and KP10. The clays with predominate Bronsted acidity (KSF, KSF/O and KP10) are preferred with KSF/O and KP10 being more preferred. Another preferred clay is K5. Other preferred acid activated clays are X-9105 and X-9107 acid washed clay catalysts marketed by Engelhard.

The term "zeolite" refers to aluminosilicates of the group IA or group IIA elements and are related to montmorillonite clays that are or have been acid activated. They consist of an infinitely extending framework of $AlO_4$ and $SiO_4$ tetrahedra linked to each other by the sharing of oxygens. The framework structure contains channels or interconnecting voids that are occupied by cations and water molecules. Acidic character is imparted or enhanced by ion exchange of the cations typically with ammonium ion and subsequent thermal deamination or calcination. The acidic sites are primarily located within the lattice pores and channels. Such zeolites include, but are not limited to, the beta type zeolites as typified by CP814E manufactured by Zeolyst International, the mordenite form of zeolites as typified by CBV21A manufactured by Zeolyst International, the Y type zeolites as typified by CBV-720 manufactured by Zeolyst International, the ZSM family of zeolites as typified by ZSM-5, and ZSM-11.

The process of the present invention is illustrated in Scheme 1 below.

Scheme 1

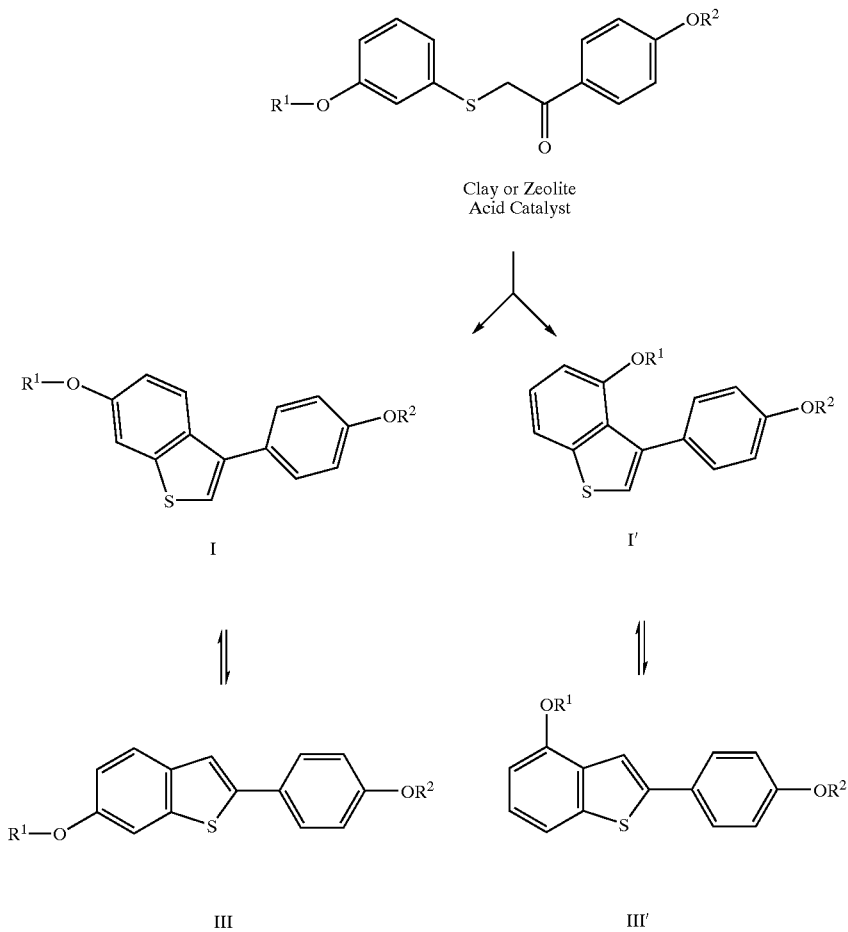

The instant process involves contacting a compound of formula II dissolved in a suitable solvent with an acid activated clay or zeolite to effect a cyclodehydration reaction affording a 3-arylbenzo[b]thiophene. As the reaction generates water, conducting the reaction at elevated temperature wherein the water generated can be removed by distillation is preferred and particularly preferred is the use of a reaction solvent which forms binary azeotropes with water. Toluene is a preferred solvent for the practice of this invention. The cyclodehydration reaction rate can be increased by increasing the amount of clay or zeolite catalyst used.

The time required to effect the overall transformation will be dependent upon the temperature at which the reactions are run and the catalyst loading. Therefore, the progress of the reactions should be monitored via conventional techniques, e.g., HPLC, to determine when the reactions are substantially complete. Monitoring the progress of chemical reactions is well within the ordinarily skilled artisan's capability. If the solvent used forms a binary water azeotrope, such as toluene, reaction completion is easily monitored by the azeotropic removal of water.

Once reaction completion is achieved the catalyst is removed by filtration of either the hot reaction mixture or after cooling. Due to the high yield, the product solution may be used as is in subsequent reactions or the product maybe isolated by conventional methods for solvent removal.

Some of the catalysts of the present invention may require activation prior to their use. For example, CP814E and CBV21A catalysts are commercially supplied in the ammonium form where ammonium ions serve as the cation counterbalancing the negative charge of the aluminum silicate lattice. These catalysts can be activated by heating which drives off ammonia converting the cation from an ammonium ion to a proton. Additionally, some catalysts are supplied containing water of hydration and may require additional activation by thermal or azeotropic drying to remove the water of hydration prior to use.

Preferred compounds of formula II for use in the present process are those where $R^1$ is hydrogen, methyl, isopropyl or benzyl, particularly hydrogen, methyl or benzyl and most particularly, hydrogen or methyl, and those where $R^2$ is methyl, isopropyl or benzyl, particularly methyl. Thus, preferred products of the above reaction include, but are not limited to, 6-hydroxy-3-(4-hydroxy phenyl)benzo[b]thiophene, 6-isopropoxy-3-(4-methoxyphenyl)benzo[b]thiophene, 6-benzyloxy-3-(4-methoxyphenyl)benzo[b]thiophene and 6-methoxy-3-(4-methoxyphenyl)benzo[b]thiophene.

As discussed above, meaningful access to compounds of formula I has heretofore been limited to use of cation exchange resins such as Amberlyst 15 and Lewis Acid catalysts such as boron trifluoride. The use of the acid catalysts claimed herein provide surprising and unexpected advantages relative to Amberlyst 15. For example, upon complete consumption of the starting material (formula II compound), the present process offers a superior 3 to 2-aryl isomer ratio. In addition, when $R^1$ and $R^2$ are both hydroxy protecting groups, the present process offers a superior 6 to 4-$OR^1$ isomer product ratio.

With a 10% weight loading of the Amberlyst 15 resin, complete consumption of a compound of formula II, where both $R^1$ and $R^2$ are methyl, is observed at 7 hours. At this time, the reaction mixture consists of 82.6% 6(3) isomer and 6.6% 6(2) isomer. Thus, 7.4% of the 6(3) isomer present has already undergone migration to the 6(2) isomer. In contrast, with the clay catalyst X-9107, loaded wet at 15%, consumption of the above starting material is observed in 3 hours. At this point, the reaction mixture consists of 95.8% 6(3) isomer and 3.9% 6(2) isomer. Thus, the extent of aryl migration using an acid of the present invention is only 3.9%.

The following table compares the 6 to 4-$OR^1$ isomer ratio observed in cyclodehydrations of a compound of formula II, where both $R^1$ and $R^2$ are methyl, employing Amberlyst 15, polyphosphoric acid, boron trifluoride etherate, and representative acid catalysts of the present invention.

TABLE 1

| Acid Catalyst | 6-Isomer | 4-Isomer |
| --- | --- | --- |
| Polyphosphoric Acid | 78% | 22% |
| Amberlyst A15 Resin | 89% | 11% |
| Boron Trifluoride | 86% | 14% |
| Bentonite Clay (X-9107) | 98% | 2% |
| Montmorillonite KP10 | 96% | 4% |
| Montmorillonite KSF | 96% | 4% |
| Montmorillonite KSF/O | 95% | 5% |
| Montmorillonite K5 | 98% | 2% |
| Montmorillonite (Aluminum pillared clay) | 92% | 8% |
| Montmorillonite K20 | 93% | 7% |
| Montmorillonite K10 | 92% | 8% |
| Montmorillonite K30 | 93% | 7% |
| Zeolyst CBV-720 | 96% | 4% |

For a compound of formula II where both $R^1$ and $R^2$ are methyl, the average in situ 6 to 4-$OR^1$ isomer ratio in twelve replicate lab trials using Amberlyst 15 was 88% to 12% while the average isolated yield of the 3-aryl isomer was 78.6% (see Example 8). Correspondingly in 3 identical scale trials using the Bentonite X-9107 catalyst the average in situ 6- to 4-$OR^1$ isomer ratio was 98% to 2% and the average isolated yield of the 3-aryl isomer was 89.7% (see Example 7).

The use of the acid catalysts claimed herein also provide advantages relative to the boron trifluoride promoted reaction. Unlike the boron trifluoride promoted process, the solvent used in the present process can be recycled. Furthermore, unlike the boron trifluoride promoted process, workup and isolation of the product prepared by the present process simply requires filtration to remove the insoluble acid catalyst. The desired product can then be further used in solution or isolated by simple solvent removal. Moreover, when $R^1$ and $R^2$ are both hydroxy protecting groups, the present process offers a superior 6 to 4-$OR^1$ isomer product ratio.

To assess potential effects of catalyst loading on the cyclodehydration reaction rate, and on the 6- to 4-$OR^1$ isomer ratio, reactions of a compound of formula II where $R^1$ is H and $R^2$ is methyl and a compound of formula II where $R^1$ and $R^2$ are both methyl, at two different concentrations in toluene (146 mM and 729 mM), were run with a 5%, 15% and 25% weight loading of Bentonite Clay X-9107 relative to the weight of substrate charged. The resulting 6 to 4-$OR^1$ isomer ratio in the cyclodehydration with both of the above formula II compounds remained constant regardless of the clay catalyst loading. The resulting 6 to 4-$OR^1$ isomer ratio was also independent of reaction concentration. Catalyst loading, as well as the reaction concentration, can impact the reaction rate with higher reaction concentrations and, in particular, higher catalyst loading resulting in faster reaction rates.

In another embodiment of the present invention, a compound of formula I, either after isolation or after preparation in situ, may be treated with polyphosphoric acid, or mixture of polyphosphoric and phosphoric acids, or treated with methanesulfonic acid to effect aryl migration and conversion to a compound of formula III as described in U.S. Pat. Nos. 4,380,635, 5,969,157 and 5,512,684, the teachings of which are hereby incorporated by reference. The improvement in 6 to 4-$OR^1$ isomer ratio discussed above, using the acids of the present invention for the cyclodehydration reaction, is reflected in isolated yields of the formula III compound.

In another preferred embodiment, a compound of formula III is acylated, optionally deprotected and optionally salified to form a compound of formula IV:

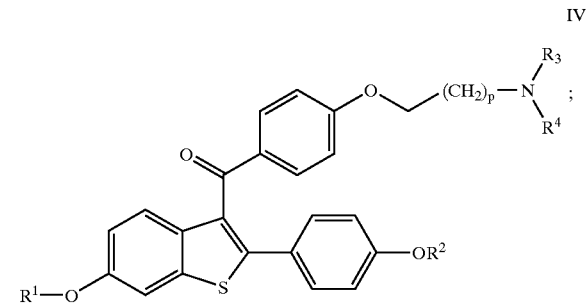

IV or a pharmaceutical salt thereof; wherein:

p is 0, 1 or 2; and $R^3$ and $R^4$ are independently $C_1$–$C_4$ alkyl, or combine together with the nitrogen to which they are attached to form a piperidinyl, pyrrolidinyl, methylpyrrolidinyl, dimethylpyrrolidinyl, morpholino, dimethylamino, diethylamino, or 1-hexamethyleneimino ring.

The acylation and optional deprotection and salification reactions may be performed essentially as described in U.S. Pat. No.'s 4,380,635, 4,418,068, 5,512,684, 5,523,416, 5,629,425, 5,731,327, 5,969,157 and 5,977,383 the teachings of each are herein incorporated by reference. The hydrochloride salt of a compound of formula IV where $R^1$ and $R^2$ is hydrogen and $R^3$ and $R^4$ combine to form a piperidinyl ring is a preferred product.

In another preferred embodiment, a compound of formula III may be 3-halogenated, S-oxidized, have the 3-halo group displaced, reduced, optionally deprotected, and optionally salified to prepare a compound of formula V:

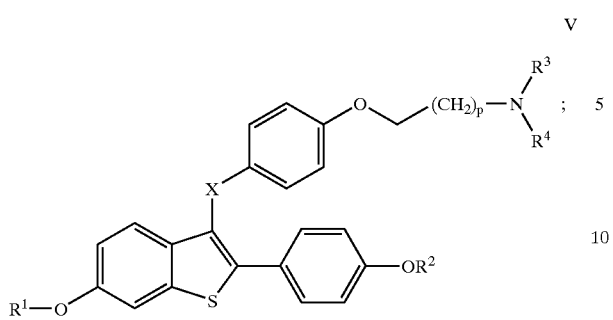

p is 0, 1 or 2;

$R^3$ and $R^4$ are independently $C_1$–$C_4$ alkyl, or combine together with the nitrogen to which they are attached to form a piperidinyl, pyrrolidinyl, methylpyrrolidinyl, dimethylpyrrolidinyl, morpholino, dimethylamino, diethylamino, or 1-hexamethyleneimino ring; and X is O or CO; or pharmaceutical salt thereof.

In a particularly preferred embodiment, a compound of formula I may be used to prepare a compound of formula VI and VII:

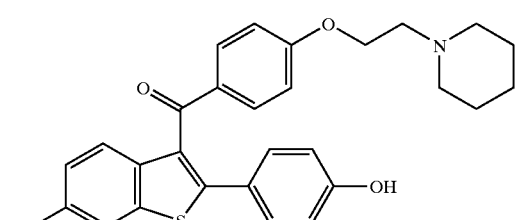

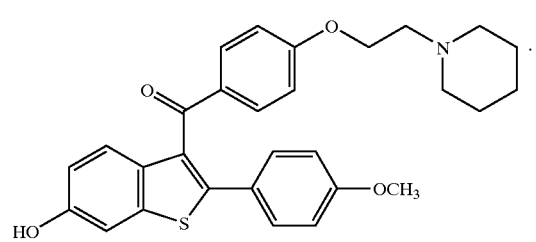

The 3-halogenation, oxidation, nucleophilic displacement of halo, reduction, and optional deprotection and salification reactions may be performed essentially as described in U.S. Pat. No. 's 5,510,357, 5,512,684, 5,523,416, 5,723,474, 5,969,157 and 5,977,383 and PCT Publication No.'s WO 01/09115 and WO 01/09116, the teachings of which are hereby incorporated by reference. The hydrochloride salt of compound of formula V where $R^1$ is hydrogen, $R^2$ is methyl, and $R^3$ and $R^4$ combine to form piperidinyl is preferred.

The acid activated clays and zeolites of the present invention are typically commercially available, however, general methods for their preparation are described in *Trans. Soc. Min. Eng.*, 282:1901–10, 1987 and references therein. Compounds of formula II are known in the art and are generally commercially available or can be prepared by methods well known in the art from readily available starting materials. The compounds of formula II may be prepared according to procedures described in U.S. Ser. No. PCT/US01/42939 filed on the same day as Ser. No. 10/415, 569.

Preparations

Preparation 1

Representative Procedure for Catalyst Activation

A 3.0 gm sample of zeolite catalyst CBV-21A was heated for approximately 4 hours at 350° C. prior to cooling and immediate use. A similar amount of zeolite catalyst CP814E was activated in a similar manner.

EXAMPLES

Example 1

6-Methoxy-3-(4-methoxyphenyl)benzo[b]thiophene

Toluene (100 ml), α-(3-methoxyphenylthio)-4-methoxyacetophenone (4.21 gm) and "acid-activated clay" (Engelhard X-9107 0.63 gm) were combined and heated to reflux. The water present in the catalyst as well as the water generated in the reaction was removed using a Dean Stark trap. The disappearance of starting material as well as the appearance of product was monitored by HPLC. After 2 hour at reflux less than 1% of the starting material remained. By HPLC the reaction mixture consisted of 96.7% 6-methoxy-3-(4-methoxyphenyl)benzo[b]thiophene, 1.1% 6-methoxy-2-(4-methoxyphenyl)benzo[b]thiophene, 2.1% 4-methoxy-3-(4-methoxyphenyl)benzo[b]thiophene and 0.1% 4-methoxy-2-(4-methoxyphenyl)benzo[b]thiophene. HPLC system used to monitor the reaction:

Column: Zorbax SB C18 4.6×150 mm, 3.5 micron
Buffer: 25 nM Phosphate Buffer, pH 2.5 (2.38 gm $KH_2PO_4$ pH to 2.5 with $H_3PO_4$ (85%/L Millipore water)
Organic: Acetonitrile
Column Temperature: 40° C.
Flow rate: 1.5 ml/min
Detection: UV, 280 nm
Injection Volume: 10 ml
Run time: 37 minutes
Gradient: Time in minutes (% ACN) 0(48); 3.3(48); 28.6(55); 32(55); 32.6(48); 37(48).

Example 2

6-Hydroxy-3-(4-methoxyphenyl)benzo[b]thiophene

Toluene (100 ml), α-(3-hydroxyphenylthio)-4-methoxyacetophenone (4.00 gm) and "acid-activated clay" (Engelhard X-9107 0.6 gm) were combined and heated to reflux. The water present in the catalyst as well as the water generated in the reaction was removed using a Dean Stark trap. The disappearance of starting material as well as the appearance of product was monitored by HPLC. After 6 hour at reflux less than 0.3% of the starting material remained. By HPLC the reaction mixture consisted of 86.2% 6-hydroxy-3-(4-methoxyphenyl)benzo[b]thiophene, 5.1% 6-hydroxy-2-(4-methoxyphenyl)benzo[b]thiophene, 8.5% 4-hydroxy-3-(4-methoxyphenyl)benzo[b]thiophene and 0.2% 4-hydroxy-2-(4-methoxyphenyl)benzo[b]thiophene. HPLC system used to monitor the reaction same as in Example 1 except gradient as follows: 0(38); 3.3(38); 28.6(45); 32(45); 32.6(38); 37(38).

Example 3

6-Methoxy-3-(4-hydroxyphenyl)benzo[b]thiophene

Toluene (100 ml), α-(3-methoxyphenylthio)-4-hydroxyacetophenone (4.00 gm) and "acid-activated clay" (Engelhard X-9107 0.6 gm) were combined and heated to reflux. The water present in the catalyst as well as the water generated in the reaction was removed using a Dean Stark trap. The disappearance of starting material as well as the appearance of product was monitored by HPLC. After 7 hour at reflux less than 1% of the starting material remained. By HPLC the reaction mixture consisted of 91.7% 6-methoxy-3-(4-hydroxyphenyl)benzo[b]thiophene, 2.2% 6-methoxy-2-(4-hydroxyphenyl)benzo[b]thiophene, 5.8% 4-methoxy-3-(4-hydroxyphenyl)benzo[b]thiophene and 0.3% 4-methoxy-2-(4-hydroxyphenyl)benzo[b]thiophene. HPLC system used to monitor the reaction same as Example 2.

Example 4

6-Hydroxy-3-(4-hydroxyphenyl)benzo[b]thiophene

Toluene (100 ml), α-(3-hydroxyphenylthio)-4-hydroxyacetophenone (3.80 gm) and "acid-activated clay" (Engelhard X-9107 0.57 gm) were combined and heated to reflux. The water present in the catalyst as well as the water generated in the reaction was removed using a Dean Stark trap. The disappearance of starting material as well as the appearance of product was monitored by HPLC. After 7 hour at reflux less than 12% of the starting material remained. By HPLC the ratio of 6 to 4-OR[1] benzo[b]thiophene isomers was 84.1% to 15.8%. HPLC system used to monitor the reaction same as Example 1 except gradient as follows: 0(28); 3.3(28); 28.6(35); 32(35); 32.6(28); 37(28).

Example 5

Catalyst Screening for Cyclodehydration of α-(3-methoxyphenylthio)-4-methoxyacetophenone Toluene (100 ml), α-(3-methoxyphenylthio)-4-methoxyacetophenone (4.21 gm) and 0.63 gm of catalyst were combined and heated to reflux. The water present in the catalyst as well as the water generated in the reaction was removed using a Dean Stark trap. The disappearance of starting material as well as the appearance of product was monitored by HPLC using the HPLC system provided in Example 1.

Example 6

Catalyst Screening for Cyclodehydration of α-(3-hydroxyphenylthio)-4-methoxyacetophenone Toluene (100 ml), α-(3-hydroxyphenylthio)-4-methoxyacetophenone (4.00 gm) and 0.6 gm of catalyst were combined and heated to reflux. The water present in the catalyst as well as the water generated in the reaction was removed using a Dean Stark trap. The disappearance of starting material as well as the appearance of product was monitored by HPLC using the HPLC system provided in Example 2. The results of this screening are indicated below in Table 2.

TABLE 2

| Catalyst | Total 6-isomer | Total 4-isomer | Reaction time (hours) |
|---|---|---|---|
| Engelhard (X-9107) | 92% | 8% | 5 |
| Montmorillonite K5 | 89% | 11% | >8 |
| Montmorillonite K10 | 82% | 18% | >8 |
| Montmorillonite K20 | 84% | 16% | >8 |
| Montmorillonite K30 | 82% | 18% | >8 |
| Montmorillonite KSF | 86% | 14% | >8 |
| Montmorillonite KSF/O | 90% | 10% | 2 |
| Montmorillonite KP10 | 90% | 10% | 7 |
| Montmorillonite (Aluminum pillared clay) | 86% | 14% | >8 |
| Zeolyst CP814E | 85% | 15% | >8 |
| Zeolyst CBV-21A | 83% | 17% | >8 |
| Zeolyst CBV-720 | 75% | 25% | 2 |

Example 7

6-Methoxy-2-(4-methoxyphenyl)benzo[b]thiophene

Toluene (300 ml), α-(3-methoxyphenylthio)-4-methoxyacetophenone (97.5 gm) and "acid-activated clay" (Engelhard X-9107 14.6 gm) were combined and heated to reflux. The water present in the catalyst as well as the water generated in the reaction was removed by using a Dean Stark trap. Heating was continued until water removal ceased. At this point the reaction mixture was held at reflux for an additional 1 hour. After a total of 4 hours the ratio of total 6- to 4-OR[1] isomers was determined using the HPLC system given in Example 1. The catalyst was removed by hot filtration and washed with 30 ml of hot toluene. To the combined filtrate and wash was added 34.5 gm of methanesulfonic acid. The resulting reaction mixture was stirred for approximately 5 hours at 85–90° C. At 85–90° C. 135 ml of heptanes was added and the resulting mixture stirred for 1 hour at 85–90° C. The reaction mixture was adjusted to 75–85° C., stirred for 3 hours and 240 ml of isopropanol slowly added followed by stirring at 80–90° C. for 30 minutes. The resulting slurry was cooled to 0–10° C., stirred for 2 hours, a mixture of 63 ml of toluene and 27 ml of isopropanol added, the solids isolated by filtration, washed with 78 ml of 4:1 toluene/isopropanol and vacuum dried at 40° C. to afford 6-methoxy-2-(4-methoxyphenyl)benzo[b]thiophene. The results of three replicate trials are shown below in Table 3.

TABLE 3

| Trial # | in situ % 6-OR[1] isomer | in situ % 4-OR[1] isomer | Isolated Yield | Purity |
|---|---|---|---|---|
| 1 | 98.0% | 2.0% | 88.1% | 99.4% |
| 2 | 97.0% | 3.0% | 91.0% | 99.0% |
| 3 | 97.5% | 2.5% | 89.9% | 99.4% |
| Average | 97.5% | 2.5% | 89.7% | 99.3% |

Example 8

6-Methoxy-2-(4-methoxyphenyl)benzo[b]thiophene

Toluene (600 ml), α-(3-methoxyphenylthio)-4-methoxyacetophenone (195 gm) and 19.5 gm of Amberlyst 15 resin were combined and heated to reflux. The water present in the resin as well as the water generated in the reaction was removed by using a Dean Stark trap. Heating was continued until water removal ceased. At this point the ratio of total 6- to 4-OR$^1$ isomers was determined using the HPLC system given in Example 1. The resin was removed by hot filtration and washed with 60 ml of hot toluene. To the combined filtrate and wash was added 69 gm of methanesulfonic acid. The resulting reaction mixture was stirred for approximately 5 hours at 85–90° C. At 85–90° C. 270 ml of heptanes was added and the resulting mixture stirred for 1 hour at 85–90° C. The reaction mixture was adjusted to 75–85° C., stirred for 3 hours and 480 ml of isopropanol slowly added followed by stirring at 80–90° C. for 30 minutes. The resulting slurry was cooled to 0–10° C. and stirred for 2 hours. A mixture of 126 ml of toluene and 54 ml of isopropanol added, the solids isolated by filtration, washed with 156 ml of 4:1 toluene/isopropanol and vacuum dried at 40° C. to afford 6-methoxy-2-(4-methoxyphenyl)benzo[b]thiophene. The results of twelve replicate trials are shown below in Table 4.

TABLE 4

| Trial # | in situ % 6-OR$^1$ isomer | in situ % 4-OR$^1$ isomer | Isolated Yield | Purity |
|---|---|---|---|---|
| 1 | 88.0% | 12.0% | 76.6% | 98.8% |
| 2 | 87.5% | 12.5% | 78.3% | 97.2% |
| 3 | 88.0% | 12.0% | 78.8% | 99.0% |
| 4 | 87.0% | 13.0% | 77.5% | 98.4% |
| 5 | 89.0% | 11.0% | 79.8% | 99.1% |
| 6 | 88.5% | 11.5% | 78.4% | 100.8% |
| 7 | 88.5% | 11.5% | 79.0% | 101.4% |
| 8 | 87.0% | 13.0% | 78.8% | 100.3% |
| 9 | 87.5% | 12.5% | 79.3% | 100.5% |
| 10 | 88.0% | 12.0% | 77.5% | 102.9% |
| 11 | 88.0% | 12.0% | 78.8% | 100.1% |
| 12 | 87.0% | 13.0% | 80.3% | 100.6% |
| Average | 87.8% | 12.2% | 78.6% | 99.9% |

We claim:

1. A process for preparing a compound of formula I:

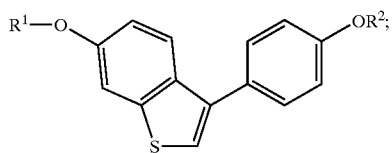

wherein:
R$^1$ and R$^2$ are independently hydrogen or a hydroxy protecting group; which comprises cyclodehydrating a compound of formula II:

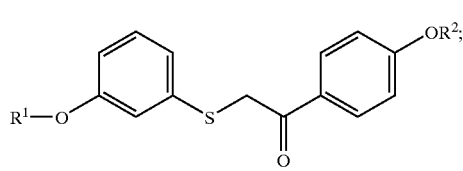

in the presence of an acid activated clay or acid activated zeolite catalyst and in the presence of a suitable solvent.

2. The process of claim 1 wherein the compound of formula II is a compound where R$^1$ is H, benzyl, methyl or isopropyl and the compound of formula III is a compound where R$^2$ is H, benzyl, methyl or isopropyl.

3. The process of claim 2 wherein the compound of formula II is a compound where R$^1$ is methyl or benzyl and wherein the compound of formula III is a compound where R$^2$ is methyl.

4. The process according to claim 3 wherein the solvent is toluene, the catalyst is Bentonite X-9107 and the process is performed at the reflux temperature of the mixture.

5. The process according to claim 3 wherein the solvent is toluene, the catalyst is K5 and the process is performed at the reflux temperature of the mixture.

6. In a process for preparing a compound of formula V:

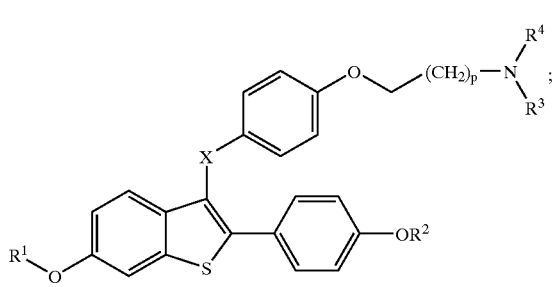

or an acid addition salt thereof;
wherein:
p is 0, 1 or 2;
R$^3$ and R$^4$ are independently C$_1$–C$_4$ alkyl, or combine together with the nitrogen to which they are attached to form a piperidinyl, pyrrolidinyl, methylpyrrolidinyl, dimethylpyrrolidinyl, morpholino, dimethylainino, diethylamino, or 1-hexamethyleneimino ring; and
X is O or CO;
the improvement which comprises the process of claim 1.

7. The process of claim 6 wherein the compound of formula V is of the formula VI:

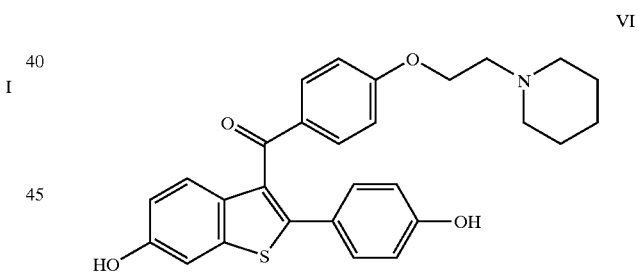

or a pharmaceutically acceptable salt thereof.

8. The process of claim 6 wherein the compound of formula V is of the formula VII:

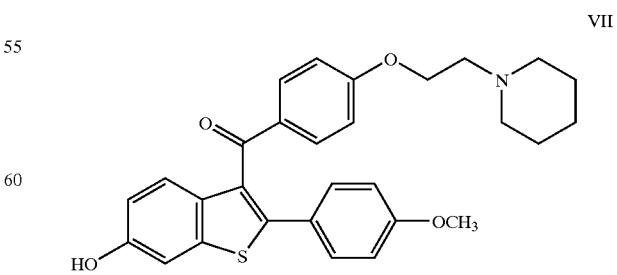

or a pharmaceutically acceptable salt thereof.

* * * * *